United States Patent [19]

Yabuki et al.

[11] Patent Number: 4,639,418

[45] Date of Patent: Jan. 27, 1987

[54] HEAT DEVELOPABLE PHOTOSENSITIVE MATERIAL

[75] Inventors: Yoshiharu Yabuki; Kozo Sato; Ken Kawata; Hiroyuki Hirai, all of Kanagawa, Japan

[73] Assignee: Fuji Photo Film Co., Ltd., Kanagawa, Japan

[21] Appl. No.: 768,282

[22] Filed: Aug. 22, 1985

[30] Foreign Application Priority Data

Aug. 22, 1984 [JP] Japan .................. 59-173161

[51] Int. Cl.$^4$ .................. G03C 1/02
[52] U.S. Cl. .................. 430/617; 430/619; 430/620; 430/955; 430/203
[58] Field of Search .................. 430/617, 619, 955, 203, 430/151, 179, 177, 620

[56] References Cited

U.S. PATENT DOCUMENTS 4,514,493  4/1985  Hirai et al. .................. 430/955

FOREIGN PATENT DOCUMENTS 0084890  8/1983  European Pat. Off. .

Primary Examiner—Won H. Louie
Attorney, Agent, or Firm—Sughrue, Mion, Zinn, Macpeak, and Seas

[57] ABSTRACT

A heat developable photosensitive material comprising a support having thereon at least one light-sensitive layer comprising light-sensitive silver halide and a binder, wherein at least one layer contains a base precursor represented by the following general formula (I):

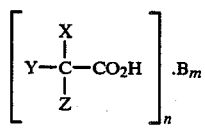

wherein at least one of X, Y and Z, which may be the same or different, represents an electron-attractive substituent selected from the group (a) consisting of a halogen atom, a nitro group, an alkysulfinyl group, an arylsulfinyl group, an acyl group, a sulfamoyl group, a sulfamoyl group substituted with an aryl group, a substituted aryl group, an alkyl group or a substituted alkyl group, a carbamoyl group, a substituted carbamoyl group, an alkoxycarbonyl group, an aryloxycarbonyl group, an aryloxysulfonyl groups

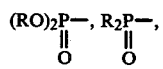

a nitroso group,

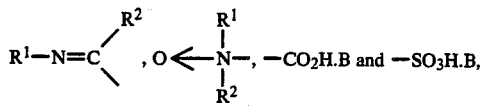

wherein B is defined as in general formula (I), and R, $R^1$ and $R^2$ each represents a hydrogen atom, an alkyl group or an aryl group, and the alkyl or aryl moiety of these groups may be further substituted;

the remainder of X, Y and Z being selected from the group (b) consisting of a hydrogen atom, an alkyl group, a cycloalkyl group, an alkenyl group, an alkynyl group, an aryl group, an aralkyl group, a silyl group, an alkoxy group, an aryloxy group, an alkylthio group, an arylthio group and a hydroxy group, wherein the alkyl and aryl moieties may be further substituted with a substituent other than a perhaloalkyl group containing up to 3 carbon atoms, provided that at least one of X, Y and Z represents a group other than a halogen or a nitro group, and any two of X, Y and Z may combine to form a ring;

B represents a mono-acidic or di-acidic base having a pKa value of at least 7 and containing not more than 12 carbon atoms; and n and m each represents 1 or 2, provided that the net charge of the compound is zero.

10 Claims, No Drawings

HEAT DEVELOPABLE PHOTOSENSITIVE MATERIAL

FIELD OF THE INVENTION

The present invention relates to a heat developable photosensitive material and, more particularly, to a heat developable photosensitive material which contains a base precursor.

BACKGROUND OF THE INVENTION

It is generally advisable to use a base in a heat developable photosensitive material for the purpose of accelerating the development caused by heat. Such bases are generally used in the form of a base precursor (i.e., a compound capable of being decomposed by heat to release a basic component) in order to increase the stability of the photosensitive material. For practical use, it is essential that the base precursor fulfills two contradictory requirements of stability at ordinary temperatures and rapid decomposition upon heating.

Specific examples of base precursors which have so far been used include ureas (described in U.S. Pat. No. 2,732,299 and Belgian Pat. No. 625,554), urea or combined use of urea and an ammonium salt of a weak acid (described in Japanese Patent Publication No. 1699/65), hexamethylenetetramine and semicarbazides (described in U.S. Pat. No. 3,157,503), combined use of triazine compounds and carboxylic acid (described in U.S. Pat. No. 3,493,375), dicyandiamide derivatives (described in U.S. Pat. No. 3,271,155), N-sulfonylureas (described in U.S. Pat. No. 3,420,665), amineimides (described in Research Disclosure, RD-15776 (1977)) and salts of pyrolyzable acids such as trichloroacetic acid (described in British Pat. No. 998,949).

However, image forming materials containing these base precursors have the serious disadvantage that they cannot satisfy the indispensable conditions of high stability upon storage at ordinary temperatures and rapid decomposition upon development processing. For this reason, such materials cannot provide high image density, or they produce images having a greatly reduced signal to noise ration because of the release of bases during storage.

SUMMARY OF THE INVENTION

Therefore, a first object of the present invention is to provide a heat developable photosensitive material which is excellent in stability during storage and enables reproduction of images of high quality.

A second object of the present invention is to provide a heat developable photosensitive material which contains a base precursor which is particularly effective in producing images of high density and reduced fog.

A third object of the present invention is to provide a heat developable photosensitive material which can produce images of high density in a short time.

The above-described objects of the present invention are attained with a heat developable photosensitive material comprising a support having thereon at least one light-sensitive layer comprising light-sensitive silver halide and a binder, wherein at least one layer contains a compound represented by the following general formula (I):

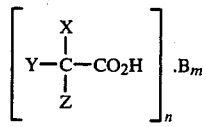

wherein at least one of X, Y and Z, which may be the same or different, represents an electron attractive substituent selected from the group (a) consisting of a halogen atom, a nitro group, an alkylsulfinyl group, an arylsulfinyl group, an acyl group, a sulfamoyl group, a substituted sulfamoyl group (examples of substituent are an aryl group, a substituted aryl group, an alkyl group or a substituted alkyl group, a carbamoyl group, a substituted carbamoyl group, an alkoxycarbonyl group, an aryloxycarbonyl group, an aryloxysulfonyl groups

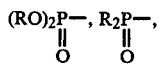

a nitroso group,

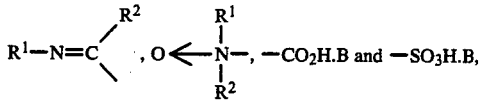

wherein B is defined as in general formula (I), and R, $R^1$ and $R^2$ each represents a hydrogen atom, an alkyl group or an aryl group, and the alkyl or aryl moiety of these groups may be further substituted.

the remainder of X, Y and Z being selected from the group (b) consisting of a hydrogen atom, an alkyl group, a cycloalkyl group, an alkenyl group, an alkynyl group, an aryl group, an aralkyl group, a silyl group, an alkoxy group, an aryloxy group, an alkylthio group, an arylthio group and a hydroxy group, wherein the alkyl and aryl moieties may be further substituted with a substituent other than a perhaloalkyl group containing up to 3 carbon atoms, provided that at least one of X, Y and Z represents a group other than a halogen or a nitro group, and any two of X, Y and Z may combine to form a ring;

B represents a mono-acidic or di-acidic base having a pKa value of at least 7 and containing not more than 12 carbon atoms; and n and m each represents 1 or 2, provided that the net charge of the compound is zero.

DETAILED DESCRIPTION OF THE INVENTION

In the group (a), substituted and unsubstituted sulfamoyl groups,

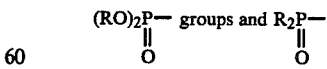

groups are particularly preferred over other groups.

The base moiety B represents an organic base, preferably one which has a pKa value of about 9 or more and a boiling point of about 100° C. or higher, and especially one which has a pKa value of 10 or more and no objectionable odor due to its substantial nonvolatility at ordinary temperatures, including guanidines, cyclic guanidines, amidines and cyclic amidines. Further, it is preferred that the base moiety B should have a strong affinity for water and that it should contain 10 or fewer carbon atoms.

Preferred examples of bases which can be employed to advantage as the base moiety B are illustrated below, although the present invention is not to be construed as being limited thereto:

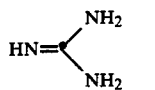 (I)

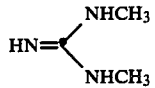 (II)

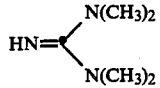 (III)

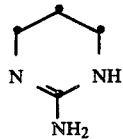 (IV)

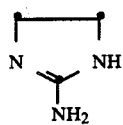 (V)

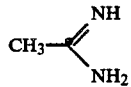 (VI)

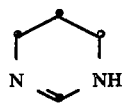 (VII)

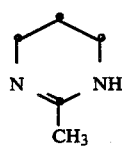 (VIII)

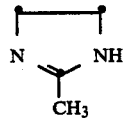 (IX)

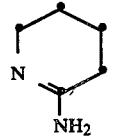 (X)

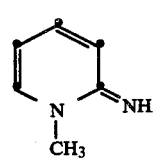 (XI)

-continued

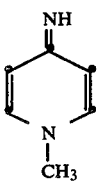 (XII)

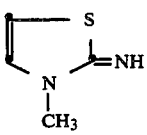 (XIII)

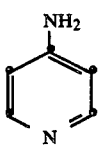 (XIV)

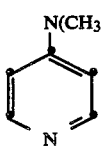 (XV)

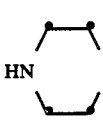 (XVI)

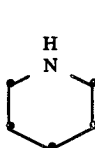 (XVII)

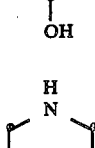 (XVIII)

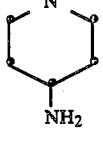 (XIX)

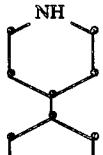

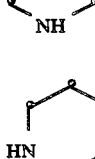 (XX)

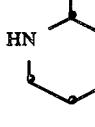

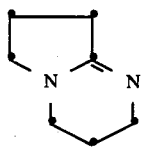 (XXI)

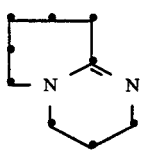 (XXII)

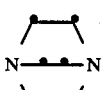 (XXIII)

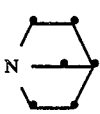 (XXIV)

(CH₃)₄NOH (XXV)

In the group (b), a hydrogen atom, an alkyl group and an aryl group are particularly preferred over other groups.

The structural characteristic of the base precursor of the present invention is that the carbon atom adjacent to the carboxyl group is substituted with an electron attractive group and thereby, the carboxyl group is made exceedingly subject to decarboxylation. However, the base precursor of the present invention is very stable at ordinary temperatures, and does not release a base component until it is heated to result in decarboxylation. For this reason, the essential requirements of a base precursor are satisfied, i.e., stability upon storage at ordinary temperatures and rapid decomposition to release a base upon development. Therefore, the use of the base precursor of the present invention enables the production of a heat developable photosensitive material which is excellent in quality and free from the defects of conventional materials.

The base precursor of the present invention can be used in a wide range, and can constitute up to about 50% of the total dry weight of coated layers of the photosensitive material, and preferably about 0.01 wt% to 40 wt% on the same basis.

Specific examples of base precursors to be used in the present invention are illustrated below. However, the present invention should not be construed as being limited to the following examples.

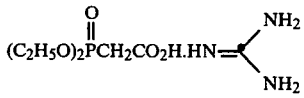 (1)

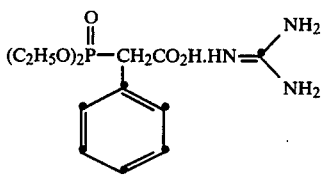 (2)

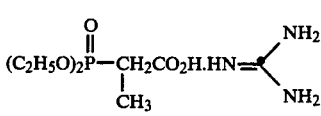 (3)

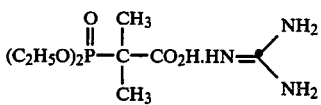 (4)

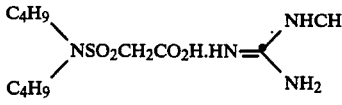 (5)

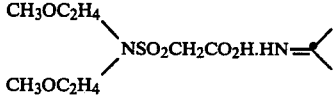 (6)

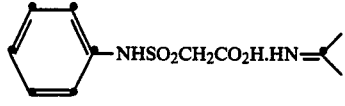 (7)

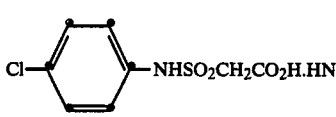 (8)

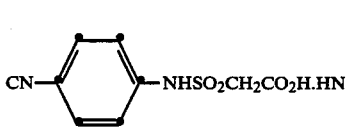 (9)

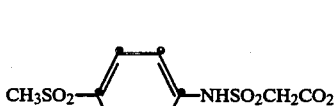 (10)

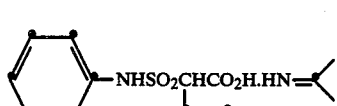 (11)

(12)

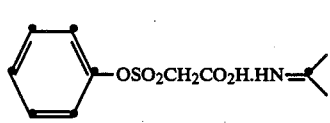 (13)

(14)

-continued

(15) 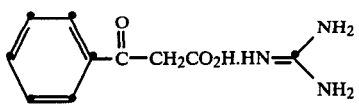

(16) 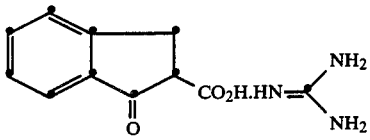

(17) 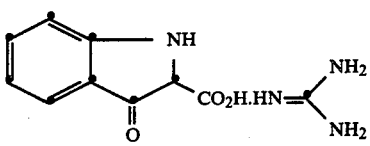

(18) 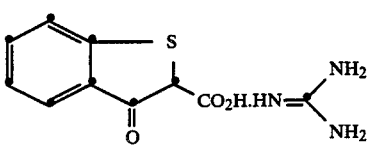

(19) 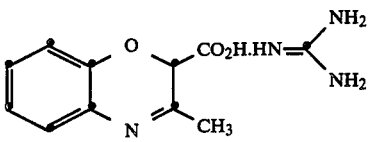

(20) 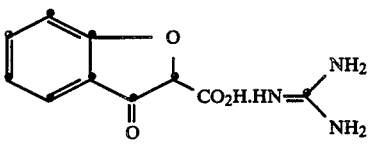

(21) 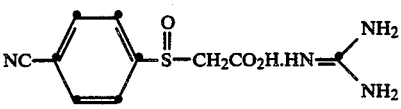

(22) 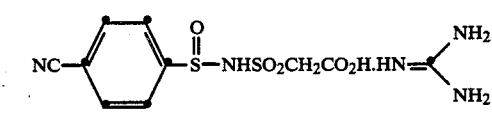

(23) 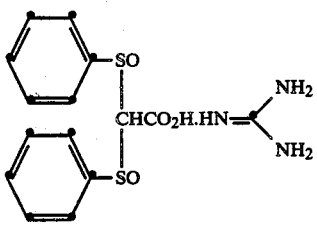

(24) 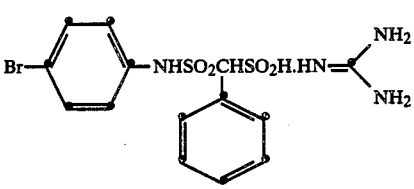

-continued

(25) 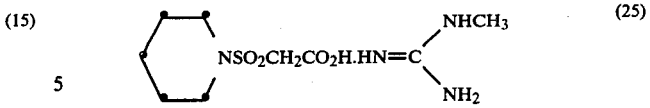

The base precursors according to the present invention can be easily synthesized.

The synthesis of the representative base precursors according to the present invention are illustrated by the following specific synthesis examples.

SYNTHESIS EXAMPLE 1

Synthesis of Compound (3):

Triethyl phosphite (18.3 g) and benzyl chloroacetate (18.5 g) were mixed, and heated at a temperature of 170° C. to 200° C. for 1 hour as chloroethane generated from the mixture was removed. The resulting reaction mixture was distilled under reduced pressure, and the distillates having boiling points ranging from 146° C. to 160° C. at a pressure of 0.5 mmHg were collected to obtain 24.5 g of colorless liquid. The liquid was converted into a carboxylic acid by cleaving benzyl ester from the reaction product through dehydrogenation. Thereafter, the resulting carboxylic acid was neutralized with guanudibe carbonate, to obtain 21.0 g of Compound (3). Melting point 185°–186° C. (decomposed).

SYNTHESIS EXAMPLE 2

Synthesis of Compound (21):

To 200 ml of dimethyl acetamide (DMAc) were added 13.9 ml of thioglycolic acid, 27.5 g of p-chlorobenzonitrile and 31.7 g of KOH. The resulting mixture was heated at a temperature of 130° C. to 140° C. over a period of 5 hours. The reaction solution was poured into diluted hydrochloric acid to precipitate 40 g of p-cyanophenylthioacetic acid. To a mixture of a 20 g portion of p-cyanophonylthioacetic acid with 100 ml of acetic acid, was added 10 ml of 35% aqueous hydrogen peroxide. The resulting mixture was heated at 60° C. for 1 hour. Upon adding water to the reaction solution, p-cyanophenylsulfinyl acetate precipitated as crystals, and these were filtered off. Yield 17.0 g, Melting Point 168°–170° C. (decomposed).

An 8 g portion of the thus obtained crystals was dissolved in 65 ml of methanol and thereto, a water solution containing 3.45 g of guanidine carbonate was added for neutralization. The resulting solution was cooled and thereby, Compound (21) precipitated as crystals, which were filtered off. Yield 7.3 g, Melting Point 193° C. (decomposed).

Base precursors according to the present invention can be synthesized using various other conventional methods. For instance, Compound (8) and Compound (9) can be synthesized according to the method described in J. Org. Chem., Vol. 34, p. 3414 (1969).

It is preferred to initially add the base precursor to the heat developable photosensitive material in the form of a salt. However, the base precursor can also be provided by adding its acid part and its base part separately to a binder to be neutralized in the binder.

The base precursor of the present invention can produce a particularly great effect when a silver halide emulsion is employed as photosensitive material. Suitable examples of silver halides which can be used in the present invention include silver chloride, silver chlorobromide, silver chloroiodide, silver bromide, silver iodobromide, silver chloroiodobromide, silver iodide and the like.

These silver halides can be prepared by various conventional methods. To cite an illustrative instance from preparation of silver iodobromide, the silver salt can be obtained by adding a silver nitrate solution to a potassium bromide solution to form silver bromide grains, and then further adding potassium iodide to the resulting solution.

Two or more kinds of silver halides in which a particle size and/or a halogen composition are different from each other may be used in mixture.

An average particle size of the silver halide used in the present invention is preferably from 0.001 $\mu$m to 10 $\mu$m and more preferably from 0.001 $\mu$m to 5 $\mu$m.

The silver halide used in the present invention may be used as is. However, it may be chemically sensitized with a chemical sensitizing agent such as compounds of sulfur, selenium or tellurium, etc., or compounds of gold, platinum, palladium, rhodium or iridium, etc., a reducing agent such as tin halide, etc., or a combination thereof. The details thereof are described in T. H. James, *The Theory of the Photographic Process*, The Fourth Edition, Chapter 5, pages 149–169.

In the present invention, a suitable coating amount of the light-sensitive silver halide is from 1 mg to 10 g/m$^2$ calculated as an amount of silver.

In accordance with a particularly preferred embodiment of the present invention, an organic silver salt oxidizing agent is present together with light-sensitive silver halide. When heated to a temperature of about 80° C. or above, preferably about 100° C. or above, in the presence of exposed silver halide, organic silver salts can form silver images by reacting with image forming substances as described hereinafter or with reducing agents present together with image forming substances as desired. Combined use of such an organic silver salt oxidizing agent and light-sensitive silver halide enables photosensitive materials to develop colors having high density.

Examples of organic silver salt oxidizing agents useful in the present invention include those described in Japanese patent application (OPI) No. 58543/83 (the term "OPI" as used herein refers to a "published unexamined Japanese Patent Application").

A silver salt of an organic compound having a carboxyl group can be used. Typical examples thereof include a silver salt of an aliphatic carboxylic acid and a silver salt of an aromatic carboxylic acid.

In addition, a silver salt of a compound containing a mercapto group or a thione group and a derivative thereof can be used.

Further, a silver salt of a compound containing an imino group can be used. Examples of these compounds include a silver salt of benzotriazole and a derivative thereof as described in Japanese Patent Publication Nos. 30270/69 and 18416/7, for example, a silver salt of benzotriazole, a silver salt of alkyl substituted benzotriazole such as a silver salt of methylbenzotriazole, etc., a silver salt of a halogen substituted benzotriazole such as a silver salt of 5-chlorobenzotriazole, etc., a silver salt of carboimidobenzotriazole such as a silver salt of butylcarboimidobenzotriazole, etc., a silver salt of 1,2,4-triazole or 1-H-tetrazole as described in U.S. Pat. No. 4,220,709, a silver salt of carbazole, a silver salt of saccharin, a silver salt of imidazole and an imidazole derivative, and the like.

Moreover, a silver salt as described in *Research Disclosure*, Vol. 170, No. 17029 (June, 1978) and an organic metal salt such as copper stearate, etc., are the organic metal salt oxidizing agent capable of being used in the present invention.

Methods of preparing these silver halide and organic silver salt oxidizing agents and manners of blending them are described in *Research Disclosure*, No. 17029, Japanese Patent Application (OPI) Nos. 32928/75 and 42529/76, U.S. Pat. No. 3,700,458, and Japanese Patent Application (OPI) Nos. 13224/74 and 17216/75.

A suitable coating amount of the light-sensitive silver halide and the organic silver salt oxidizing agent employed in the present invention is in a total of from 50 mg/m$^2$ to 10 g/m$^2$ calculated as an amount of silver.

When used together with a spectrally sensitized light-sensitive silver halide emulsion, the base precursor of the present invention is particularly effective, and enhances image density to a particularly great extent.

Spectral sensitization can be effected using methine dyes or other dyes. Dyes which can be used for spectral sensitization include cyanine dyes, merocyanine dyes, complex cyanine dyes, complex merocyanine dyes, holopolar cyanine dyes, hemicyanine dyes, styryl dyes and hemioxonol dyes. Especially useful dyes are cyanine dyes, merocyanine dyes and complex merocyanine dyes. Any nuclei conventionally used in cyanine dyes can be the base heterocyclic nuclei of these dyes as used in the present invention, including basic heterocyclic nuclei such as pyrroline, oxazoline, thiazoline, pyrrole, oxazole, thiazole, selenazoline, imidazole, tetrazole, pyridine and like nuclei; nuclei formed by fusing together one of the above-described nuclei and an alicyclic hydrocarbon ring; and nuclei formed by fusing together one of the above-described nuclei and an aromatic hydrocarbon ring. Specific examples of these nuclei include indolenine, benzindolenine, indole, benzoxazole, naphthoxazole, benzothiazole, naphthothiazole, benzoselenazole, benzoimidazole, quinoline and like nuclei. Each of these nuclei may be substituted at its carbon atoms.

The merocyanine and complex merocyanine dyes can contain 5- or 6-membered heterocyclic nuclei, such as pyrazoline-5-one, thiohydantoin, 2-thioxazolidine-2,4-dione, thiazolidine-2,4-dione, rhodanine, thiobarbituric acid and like nuclei, as ketomethylene structure-containing nuclei.

These sensitizing dyes can be employed invididually, and can also be employed in combination thereof. A combination of sensitizing dyes is often used, particularly for the purpose of supersensitization. Representative examples thereof are described in U.S. Pat. Nos. 2,688,545, 2,977,229, 3,397,060, 3,522,052, 3,527,641, 3,617,293, 3,628,964, 3,666,480, 3,672,898, 3,679,428, 3,703,377, 3,769,301, 3,814,609, 3,837,862 and 4,026,707, British Pat. Nos. 1,344,281 and 1,507,803, Japanese Patent Publication Nos. 4936/68 and 12375/78, Japanese Patent Application (OPI) Nos. 110618/77 and 109925/77, etc.

The sensitizing dyes may be present in the emulsion together with dyes which themselves do not give rise to spectrally sensitizing effects but exhibit a supersensitizing effect or materials which do not substantially absorb visible light but exhibit a supersensitizing effect. For example, aminostilbene compounds substituted with a nitrogen-containing heterocyclic group (e.g., those described in U.S. Pat. Nos. 2,933,390 and 3,635,721), aromatic organic acid-formaldehyde condensates (e.g., those described in U.S. Pat. No. 3,743,510), cadmium salts, azaindene compounds, etc., can be present. The combinations described in U.S. Pat. Nos. 3,615,613, 3,615,641, 3,617,295 and 3,635,721 are particularly useful.

Such a sensitizing dye is used in an amount ranging from about 0.001 g to 20 g, particularly from about 0.01 g to 2 g, per 100 g of silver in the emulsion.

Besides using silver as an image forming substance, the present invention can employ a wide variety of other image forming substances according to various methods.

Such other image forming substances include couplers which can form color images by coupling with oxidation products of developers used in the widely known liquid development processing. Suitable examples of magenta couplers include 5-pyrazolone couplers, pyrazolobenzimidazole couplers, cyanoacetylcoumarone couplers, and open-chain acylacetonitrile couplers. Suitable examples of yellow couplers include acylacetamide couplers (e.g., benzoylacetoanilides, and pivaloylacetoanilides). Suitable examples of cyan couplers include naphthol couplers and phenol couplers. It is desired that these couplers should be rendered nondiffusible by a hydrophobic group functioning as a ballast group, or should have a polymerized form. These couplers may be either two-equivalent or four-equivalent to silver ion. Colored couplers having a color correction effect, or couplers capable of releasing a development inhibitor upon development (i.e., "DIR couplers") may be included.

Another example of suitable image forming substances is dyes for forming positive dye images using a light-sensitive silver dye bleach process. Specific examples of such dyes include those described in *Research Disclosure*, pp. 30–32 (RD-14433) (April, 1976), *Research Disclosure*, pp. 14–15 (RD-15227) (December, 1976), U.S. Pat. No. 4,235,957, and leuco dyes described in U.S. Pat. Nos. 3,985,565 and 4,022,617.

In addition, dyes into which nitrogen-containing heterocyclic nuclei are introduced described in *Research Disclosure*, pp. 54–58 (RD-16966) (May, 1978), can be employed as image forming substances.

Further, dye providing substances which release mobile dyes by a coupling reaction with reducing agents oxidized by a redox reaction with silver halides or organic silver salts under high temperatures, described in European Pat. Nos. 67,455 and 79,056, and West German Pat. No. 3,217,853, and dye providing substances which undergo a redox reaction with silver halides or organic silver salts under high temperatures to release mobile dyes, described in European Pat. Nos. 66,282 and and 76,492, West German Pat. No. 3,215,485, and Japanese Patent Application (OPI) Nos. 154445/84 and 152440/84, can be employed.

Dye providing substances which can be employed in the above-described methods are described in greater detail below.

Dye providing substances which preferably can be used in these methods are represented by the following general formula (CI):

$$(Dye-X)_{\overline{q}} Y \qquad (CI)$$

wherein q represents 1 or 2, and when q is 2, the two (Dye—X) moieties may be the same or different.

Dye represents a dye which becomes mobile when released from the molecule, preferably one which contains a hydrophilic group. Specific examples of dyes which can be used in the dye providing substances include azo dyes, azomethine dyes, anthraquinone dyes, naphthoquinone dyes, styryl dyes, nitro dyes, quinoline dyes, carbonyl dyes, and phthalocyanine dyes. These dyes can also be used in an altered form such that they can return their original colors upon development processing, specifically in a temporarily blue-shifted form.

More specifically, dyes described in European Pat. No. 76,492 can be utilized herein.

X represents a simple bonding or a linkage group, with specific examples including an $$-\underset{\underset{R}{|}}{N}-$$

group (wherein R represents a hydrogen atom, an alkyl group or a substituted alkyl group), an —SO$_2$— group, a —CO— group, an alkylene group, a substituted alkylene group, a phenylene group, a substituted phenylene group, a naphthylene group, a substituted naphthylene group, an oxygen atom, an —SO— group, and groups formed by combining two or more of these groups.

Y represents a group capable of releasing Dye in correspondence or counter-correspondence to the light-sensitive silver salt having a latent image in an imagewise distribution, and further providing a difference in diffusibility between the released dye and the compound represented by Dye—X—Y.

In the following, preferred embodiments of Y in the formula (CI) are described in greater detail.

In one embodiment, Y is selected so that the compound represented by the general formula (CI) is an image forming nondiffusible compound which is oxidized as a result of development, thereby undergoing self-cleavage and releasing a diffusible dye.

An example of Y which is effective for compounds of this type is an N-substituted sulfamoyl group. For example, a group represented by formula (CII) is illustrated for Y.

$$\text{(Ball)}_b \underset{\beta}{\overset{\alpha}{\diagdown}} \underset{NHSO_2-}{\diagup}$$

(CII)

wherein $\beta$ represents non-metallic atoms necessary for forming a benzene ring, which may optionally be condensed with a carbon ring or a hetero ring to form, for example, a naphthalene ring, a quinoline ring, a 5,6,7,8-tetrahydronaphthalene ring, a chroman ring or the like;

$\alpha$ represents a group of —OG$^{11}$ or —NHG$^{12}$ (wherein G$^{11}$ represents hydrogen or a group which forms a hydroxyl group upon being hydrolyzed, and G$^{12}$ represents hydrogen, an alkyl group containing 1 to 22 carbon atoms or a hydrolyzable group);

Ball represents a ballast group; and b represents an integer of 0, 1 or 2.

Specific examples of this type of Y are described in Japanese Patent Application (OPI) Nos. 33826/73 and 50736/78.

Other examples of Y suited for this type of compound are those represented by the following general formula (CIII):

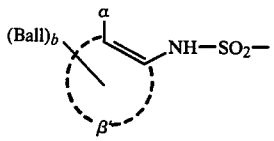
(CIII)

wherein Ball, α and b are the same as defined with (CII), β' represents atoms necessary for forming a carbon ring, e.g., a benzene ring which may be condensed with another carbon ring or a hetero ring to form a naphthalene ring, quinoline ring, 5,6,7,8-tetrahydronaphthalene ring, chroman ring or the like. Specific examples of this type of Y are described in Japanese Patent Application (OPI) Nos. 113624/76, 12642/81, 16131/81, 16130/81, 4043/82 and 650/82, and U.S. Pat. No. 4,053,312.

Further examples of Y suited for this type of compound are those represented by the following formula (CIV):

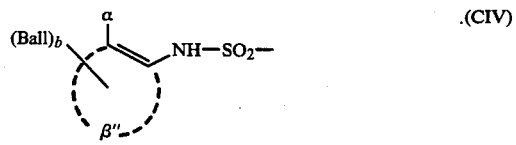
(CIV)

wherein Ball, α, and b are the same as defined with formula (CII), and β" represents atoms necessary for forming a hetero ring such as a pyrazole ring, a pyridine ring or the like, said hetero ring being optionally bound to a carbon ring or a hetero ring. Specific examples of this type of Y are described in Japanese Patent Application (OPI) No. 104343/76.

Still further examples of Y suited for this type of compound are those represented by the following formula (CV):

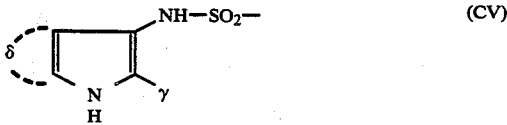
(CV)

wherein γ preferably represents hydrogen, a substituted or unsubstituted alkyl, aryl or heterocyclic group, or —CO—$G^{21}$; $G^{21}$ represents —$OG^{22}$, —S—$G^{22}$ or

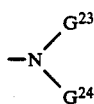

(wherein $G^{22}$ represents hydrogen, an alkyl group, a cycloalkyl group or an aryl group, $G^{23}$ is the same as defined for said $G^{22}$, or $G^{23}$ represents an acyl group derived from an aliphatic or aromatic carboxylic or sulfonic acid, and $G^{24}$ represents hydrogen atom or an unsubstituted or substituted alkyl group); and δ represents a residue necessary for completing a condensed benzene ring.

Specific examples of this type of Y are described in Japanese Patent Application (OPI) Nos. 104343/76, 46730/78, 130122/79 and 85055/82.

Still further examples of Y suited for this type of compound are those represented by the formula (CVI):

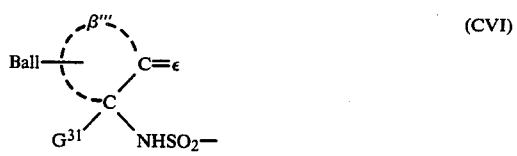
(CVI)

wherein Ball is the same as defined with the formula (CII); ε represents an oxygen atom or =$NG^{32}$ (wherein $G^{32}$ represents a hydroxyl or an optionally substituted amino group) (examples of $H_2N$—$G^{32}$ to be used for forming the group of =$NH^{32}$ including hydroxylamine, hydrazines, semicarbazides, thiosemicarbazides, etc.); β''' represents a saturated or unsaturated nonaromatic 5-, 6- or 7-membered hydrocarbon ring; and $G^{31}$ represents hydrogen or a halogen atom (e.g., a fluorine atom, a chlorine atom, a bromine atom, etc.).

Specific examples of this type of Y are described in Japanese Patent Application (OPI) Nos. 3819/78 and 48534/79.

Other examples of Y of this type of compound are described in Japanese Patent Publication Nos. 32129/73, 39165/73, Japanese Patent Application (OPI) No. 64436/74, U.S. Pat. No. 3,443,934, etc.

Still further examples of Y are those represented by the following formula (CVII):

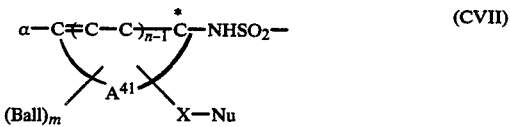
(CVII)

wherein α represents —$OR^{41}$ or —$NHR^{42}$; $R^{41}$ represents hydrogen or a hydrolyzable component; $R^{42}$ represents hydrogen, an alkyl group containing 1 to 50 carbon atoms or a hydrolyzable group; $A^{41}$ represents atoms necessary for forming an aromatic ring; Ball represents an organic immobile group existing on the aromatic ring, with Ball's being the same or different from each other; m represents an integer of 1 or 2; X represents a divalent organic group having 1 to 8 atoms, with the nucleophilic group (Nu) and an electrophilic center (asterisked carbon atom) formed by oxidation forming a 5- to 12-membered ring; Nu represents a nucleophilic group; n represents an integer of 1 or 2; and α may be the same as defined with the above-described formula (CII). Specific examples of this type of Y are described in Japanese Patent Application (OPI) No. 20735/82.

In another embodiment, Y is selected so that the compound represented by the general formula (CI) is an image forming nondiffusible compound which releases a diffusible dye in the presence of a base as a result of self cyclization or the like but which, when reacted with an oxidation product of a developing agent, substantially never releases the dye.

Examples of Y effective for this type of compound are those which are represented by the formula (CVIII):

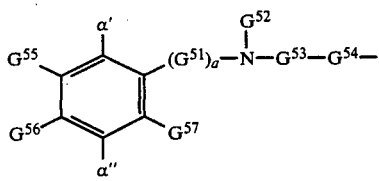

wherein α' represents an oxidizable nucleophilic group (e.g., a hydroxyl group, a primary or secondary amino group, a hydroxyamino group, a sulfonamido group or the like), or a precursor thereof;

α" represents a dialkylamino group or an optional group defined for α';

$G^{51}$ represents an alkylene group having 1 to 3 carbon atoms;

a represents 0 or 1;

$G^{52}$ represents a substituted or unsubstituted alkyl group having 1 to 40 carbon atoms or a substituted or unsubstituted aryl group having 6 to 40 carbon atoms;

$G^{53}$ represents an electrophilic group such as —CO—, or —CS—;

$G^{54}$ represents an oxygen atom, a sulfur atom, a selenium atom, a nitrogen atom or the like and, when $G^{54}$ represents a nitrogen atom, it has hydrogen or may be substituted by an alkyl or substituted alkyl group having 1 to 10 carbon atoms or an aromatic residue having 6 to 20 carbon atoms; and $G^{55}$, $G^{56}$ and $G^{57}$ each represents hydrogen, a halogen atom, a carbonyl group, a sulfamoyl group, a sulfonamido group, an alkyloxy group having 1 to 40 carbon atoms or an optional group defined for $G^{52}$, $G^{55}$ and $G^{56}$ may form a 5- to 7-membered ring, and $G^{56}$ may represent

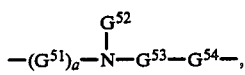

with the proviso that at least one of $G^{52}$, $G^{55}$, $G^{56}$ and $G^{57}$ represents a ballast group. Specific examples of this type of Y are described in Japanese Patent Application (OPI) No. 63618/76.

Further examples of Y suited for this type of compound are those which are represented by the following formulae (CIX) and (CX):

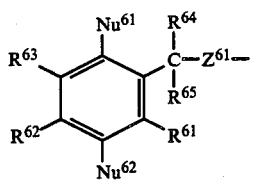

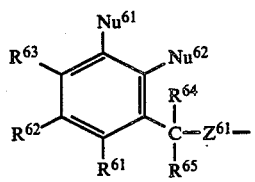

wherein $Nu^{61}$ and $Nu^{62}$, which may be the same or different, each represents a nucleophilic group or a precursor thereof; $Z^{61}$ represents a divalent atom group which is electrically negative with respect to the carbon atom substituted by $R^{64}$ and $R^{65}$; $R^{61}$, $R^{62}$, and $R^{63}$ each represents hydrogen, a halogen atom, an alkyl group, an alkoxy group or an acylamino group or, when located at adjacent positions on the ring, $R^{61}$ and $R^{62}$ may form a condensed ring together with the rest of the molecule, or $R^{62}$ and $R^{63}$ may form a condensed ring together with the rest of the molecule; $R^{64}$ and $R^{65}$, which may be the same or different, each represents hydrogen, a hydrocarbon group or a substituted hydrocarbon group; with at least one of the substituents, $R^{61}$, $R^{62}$, $R^{63}$, $R^{64}$ and $R^{65}$ having a ballast group, Ball, of an enough size so as to render the above-described compounds immobile. Specific examples of this type of Y are described in Japanese Patent Application (OPI) Nos. 69033/78 and 130927/79.

Further examples of Y suited for this type of compounds are those which are represented by the formula of (CXI):

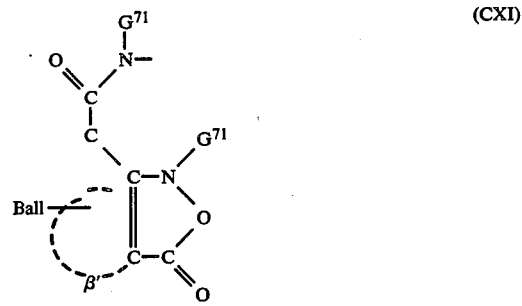

wherein Ball and β' are the same as defined for those in formula (CIII), and $G^{71}$ represents an alkyl group (including a substituted alkyl group). Specific examples of this type of Y are described in Japanese Patent Application (OPI) Nos. 111628/74 and 4819/77.

In still another embodiment, Y is selected so that the compound represented by the general formula (CI) is an image forming nondiffusible compound which itself does not release any dye but, upon reaction with a reducing agent, releases a dye. With these compounds, compounds which mediate the redox reaction (called electron donors) are preferably used in combination.

Examples of Y effective for this type of compounds are those represented by the formula (CXII):

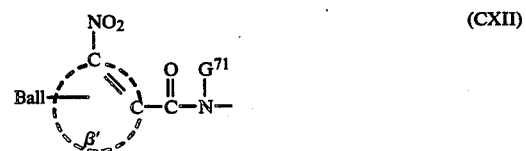

wherein Ball and β' are the same as defined for those in the general formula (CIII), and $G^{71}$ represents an alkyl group (including a substituted alkyl group). Specific examples of this type of Y are described in Japanese Patent Application (OPI) Nos. 35533/78 and 110827/78.

Further examples of Y suited for this type of compound are those which are represented by the formula (CXIII):

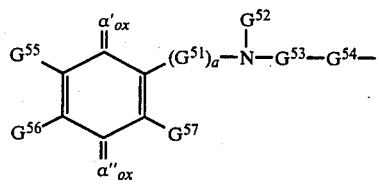
(CXIII)

wherein $\alpha'_{ox}$ and $\alpha''_{ox}$ represent groups capable of giving $\alpha'$ and $\alpha''$, respectively, upon reduction, and $\alpha'$, $\alpha''$, $G^{51}$, $G^{52}$, $G^{53}$, $G^{54}$, $G^{55}$, $G^{56}$, $G^{57}$ and a are the same as defined with respect to formula (CVIII). Specific examples of Y described above are described in Japanese Patent Application (OPI) No. 110827/78, U.S. Pat. Nos. 4,356,249 and 4,358,525.

Further examples of Y suited for this type of compound are those which are represented by the formulae (CXIV-A) and (CXIV-B):

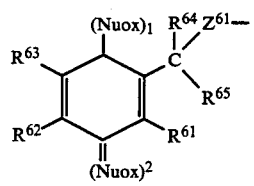
(CXIV-A)

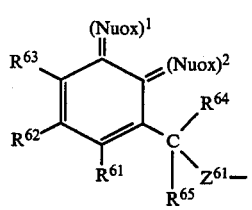
(CXIV-B)

wherein (Nuox)$^1$ and (Nuox)$^2$, which may be the same or different, each represents an oxidized nucleophilic group, and other notations are the same as defined with respect to the formulae (CIX) and (CX). Specific examples of this type of Y are described in Japanese Patent Application (OPI) Nos. 130927/79 and 164342/81.

The publicly known documents having been referred to with respect to (CXII), (CXIII), (CXIV-A) and (CXV-B) describe electron donors to be used in combination.

In a further embodiment, Y is selected so that the compound represented by the general formula (CI) is a LDA compound (Linked Donor Acceptor Compound). The compound is an image forming nondiffusible compound which causes donor-acceptor reaction in the presence of a base to release a diffusible dye but, upon reaction with an oxidation product of a developing agent, it substantially does not release the dye any more.

Examples of Y effective for this type of compound are those represented by the formula of (CXV) (specific examples thereof being described in Japanese Patent Application (OPI) No. 60289/83):

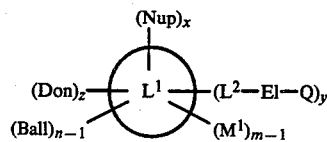
(CXV)

wherein n, x, y, and z each represents 1 or 2; m represents an integer of 1 or more; Don represents a group containing an electron donor or its precursor moiety; L$^1$ represents an organic group linking Nup to —El—Q or Don; Nup represents a precursor of a nucleophilic group; El represents an electrophilic center; Q represents a divalent group; Ball represents a ballast group; L$^2$ represents a linking group; and M$^1$ represents an optional substituent.

The ballast groups is an organic ballast group which can render the dye image forming compound nondiffusible, and is preferably a group containing a C$_{8-32}$ hydrophobic group. Such organic ballast group is bound to the dye image forming compound directly or through a linking group (e.g., an imino bond, an ether bond, a thioether bond, a carbonamido bond, a sulfonamido bond, a ureido bond, an ester bond, an imido bond, a carbamoyl bond, a sulfamoyl bond, etc., and combination thereof).

Two or more kinds of the dye providing substances can be employed together. In such a case two or more kinds of the dye providing substances may be used together in order to provide the same hue or in order to reproduce black color.

Specific examples of image forming compounds which can be used in the present invention are described in the patents cited hereinbefore. Since length prevents illustrating all preferred examples thereof, only a portion thereof is described hereinafter. Specific examples of the dye providing substances represented by general formula (CI) are set forth below.

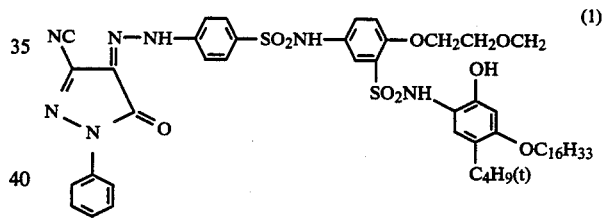
(1)

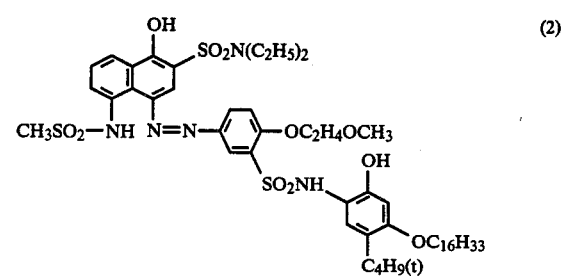
(2)

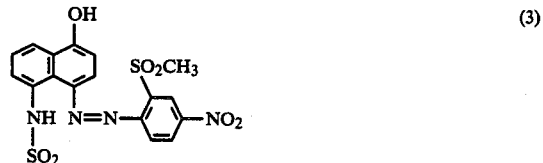

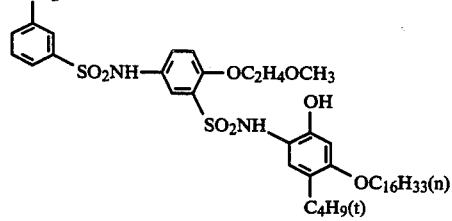
(3)

-continued
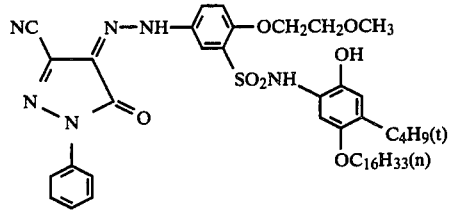 (4)
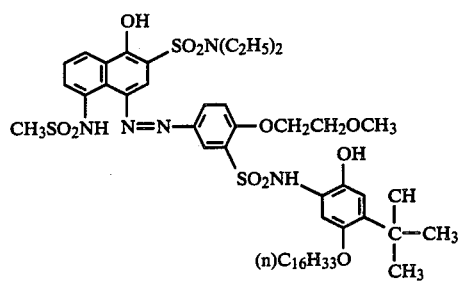 (5)
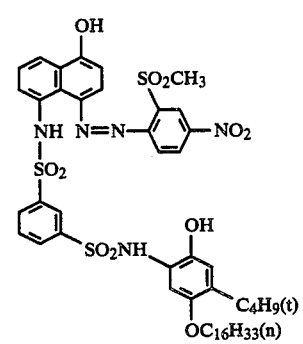 (6)
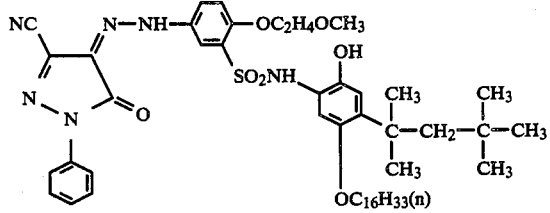 (7)
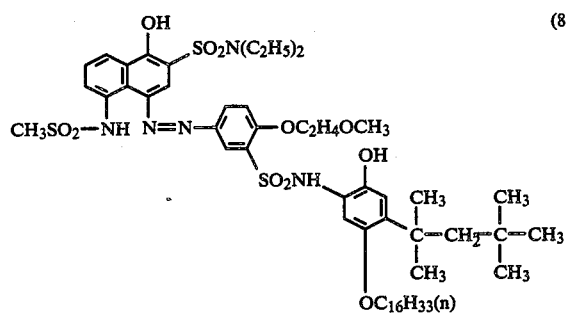 (8)
-continued
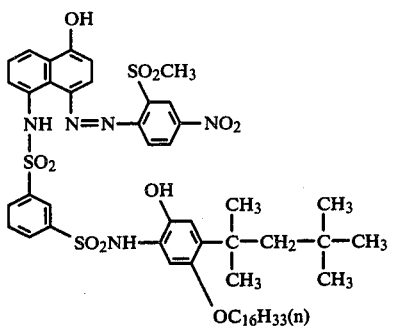 (9)
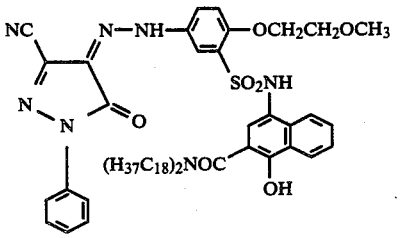 (10)
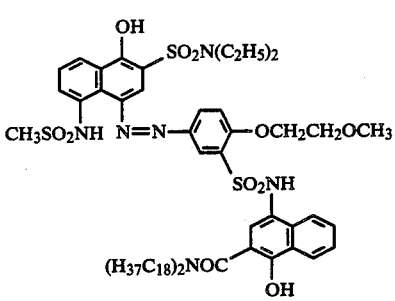 (11)
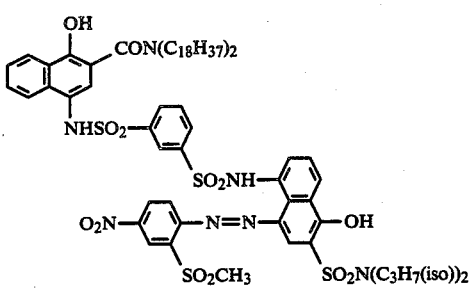 (12)
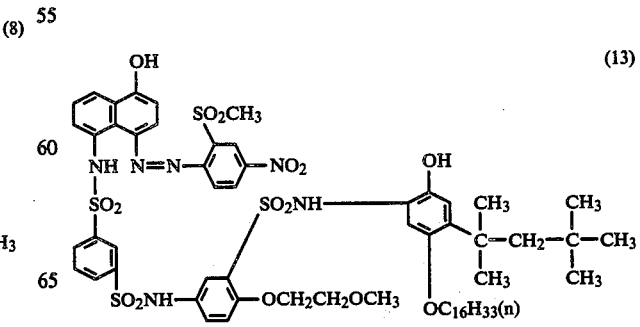 (13)

-continued

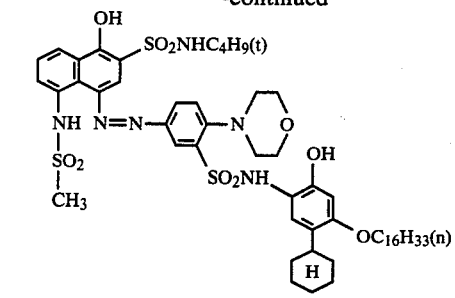

(14)

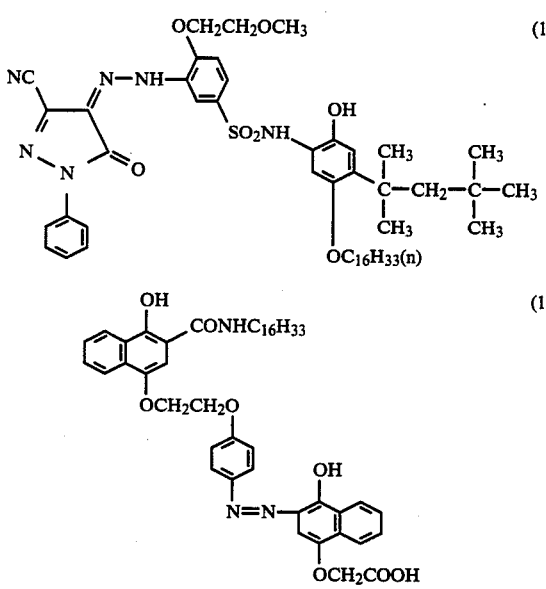

(15)

(16)

The above described compounds are only given as examples and the present invention should not be construed as being limited thereto.

Many of the above-described substances can produce imagewise distributions of mobile dyes in correspondence to exposure in a photosensitive material upon heat development. Methods for producing images by the transfer of these image dyes into a dye fixing material (i.e., "diffusion transfer" methods) are described in the patent cited above, and Japanese Patent Application (OPI) Nos. 168439/84 and 182447/84.

The dye providing substance used in the present invention can be introduced into a layer of the photosensitive material by known methods such as a method as described in U.S. Pat. No. 2,322,027. In this case, an organic solvent having a high boiling point or an organic solvent having a low boiling point as described below can be used. For example, the dye providing substance is dispersed in a hydrophilic colloid after dissolved in an organic solvent having a high boiling point, for example, a phthalic acid alkyl ester (for example, dibutyl phthalate, dioctyl phthalate, etc.), a phosphoric acid ester (for example, diphenyl phosphate, triphenyl phosphate, tricresyl phosphate, dioctylbutyl phosphate, etc.), a citric acid ester (for example, tributyl acetylcitrate, etc.), a benzoic acid ester (for example, octyl benzoate, etc.), an alkylamide (for example, diethyl laurylamide, etc.), an aliphatic acid ester (for example, dibutoxyethyl succinate, dioctyl azelate, etc.), a trimesic acid ester (for example, tributyl trimesate, etc.), etc., or an organic solvent having a boiling point of about 30° C. to 160° C., for example, a lower alkyl acetate such as ethyl acetate, butyl acetate, etc., ethyl propionate, secondary butyl alcohol, methyl isobutyl ketone, α-ethoxyethyl acetate, methyl cellosolve acetate, cyclohexanone, etc. The above described organic solvents having a high boiling point and organic solvents having a low boiling point may be used as a mixture thereof.

Further, it is possible to use a dispersion method using a polymer as described in Japanese Patent Publication No. 39853/76 and Japanese Patent Application (OPI) No. 59943/76. Moreover, various surface active agents can be used when the dye providing substance is dispersed in a hydrophilic colloid. For this purpose, the surface active agents will illustrated in other part of the specification can be used.

In the present invention, if necessary, a reducing agent may be used.

The reducing agents used in the present invention include the following compounds.

Hydroquinone compounds (for example, hydroquinone, 2,5-dichlorohydroquinone, 2-chlorohydroquinone, etc.), aminophenol compounds (for example, 4-aminophenol, N-methylaminophenol, 3-methyl-4-aminophenol, 3,5-dibromoaminophenol, etc.), catechol compounds (for example, catechol, 4-cyclohexylcatechol, 3-methoxycatechol, 4-(N-octadecylamino)catechol, etc.), phenylenediamine compounds (for example, N,N-diethyl-p-phenylenediamine, 3-methyl-N,N-diethyl-p-phenylenediamine, 3-methoxy-N-ethyl-N-ethoxy-p-phenylenediamine, N,N,N',N'-tetramethyl-p-phenylenediamine, etc.).

Various combinations of developing agents as described in U.S. Pat. No. 3,039,869 can also be used.

In the present invention, an amount of the reducing agent added is from 0.01 mol to 20 mols per mol of silver and more preferably from 0.1 mol to 10 mols per mol of silver.

The binder which can be used in the present invention can be employed individually or in a combination thereof. A hydrophilic binder can be used as the binder according to the present invention. The typical hydrophilic binder is a transparent or translucent hydrophilic colloid, examples of which include a natural substance, for example, protein such as gelatin, a gelatin derivative, a cellulose derivative, etc., a polysaccharide such as starch, gum arabic, etc., and a synthetic polymer, for example, a water-soluble polyvinyl compound such as polyvinyl alcohol, polyvinyl pyrrolidone, acrylamide polymer, etc. Another example of the synthetic polymer compound is a dispersed vinyl compound in a latex form which is used for the purpose of increasing dimensional stability of a photosensitive material.

Further, in the present invention, it is possible to use a compound which activates development simultaneously while stabilizing the image. Particularly, it is preferred to use isothiuroniums including 2-hydroxyethylisothiuronium trichloroacetate as described in U.S. Pat. No. 3,301,678, bisisothiuroniums including 1,8-(3,6-dioxaoctane)-bis(isothiuronium trifluoroacetate), etc., as described in U.S. Pat. No. 3,669,670, thiol compounds as described in West German Patent Application (OLS) No. 2,162,714, thiazolium compounds such as 2-amino-2-thiazolium trichloroacetate, 2-amino-5-bromoethyl-2-thiazolium trichloroacetate, etc., as described in U.S. Pat. No. 4,012,260, compounds having α-sulfonyl acetate as an acid part such as bis(2-amino-2-thiazolium)methylenebis(sulfonylacetate), 2-amino-2-thiazolium phenylsulfonylacetate, etc., as described in U.S. Pat. No. 4,060,420, and compounds having 2-carboxycarboxamide as an acid part as described in U.S. Pat. No. 4,088,496.

The photosensitive material of the present invention can contain a toning agent as occasion arises. Effective toning agents are 1,2,4-triazoles, 1H-tetrazoles, thiouracils, 1,3,4-thiadiazoles, and like compounds. Examples of preferred toning agents include 5-amino-1,3,4-thiadiazole-2-thiol, 3-mercapto-1,2,4-triazole, bis(dimethylcarbamyl)disulfide, 6-methylthiouracil, 1-phenyl-2-tetrazoline-5-thione, and the like. Particularly effective toning agents are compounds which can impart a black color tone to images.

The content of such a toning agent as described above, though depending upon the kind of a heat developable photosensitive material used, processing conditions, desired images and various other factors, generally ranges from about 0.001 to 0.1 mol per mol of silver in the photosensitive material.

In the present invention, it is particularly preferred to use various bases or base precursors as dye releasing assistants.

The bases or precursors thereof can be used in a photosensitive material and/or a dye fixing material. In the case of incorporating them in a photosensitive material, it is particularly advantageous to use base precursors, and to add them to the layer containing the acid precursors or a layer adjacent to the layer containing the acid precursors. The term "base precursor" used herein means a substance which releases a base component by heating to a temperature of development, where the base component released may be any inorganic base or organic base.

As examples of preferred bases, there are, as inorganic bases, hydroxides, secondary or tertiary phosphates, borates, carbonates, quinolinates and metaborates of alkali metals or alkaline earth metals; ammonium hydroxide; quaternary alkylammonium hydroxide; and other metal hydroxides; etc., and, as organic bases, aliphatic amines, aromatic amines, heterocyclic amines, amidines, cyclic amidines, guanidines, cyclic guanidines, etc. In the present invention, compounds having a pKa value of 8 or more are particularly useful.

As the base precursors, substances which undergo reaction by heating to release a base, such as salts of an organic acid which is decarboxylated by heating to undergo decomposition and yield a base, or compounds which are decomposed by Lossen rearrangement or Beckmann rearrangement to release an amine, are used.

As preferred base precursors, there are precursors of the above described organic bases. For example, there are salts of thermally decomposable organic acids such as trichloroacetic acid, propiolic acid, cyanoacetic acid, sulfonylacetic acid, acetoacetic acid, etc., and salts of 2-carboxycarboxamide as described in U.S. Pat. No. 4,088,496, etc.

Specific examples of preferred bases are set forth below, but the present invention should not be construed as being limited to these compounds.

Lithium hydroxide, sodium hydroxide, potassium hydroxide, barium hydroxide, sodium carbonate, potassium carbonate, sodium quinolinate, potassium quniolinate, sodium secondary phosphate, potassium secondary phosphate, sodium tertiary phosphate, potassium tertiary phosphate, sodium pyrophosphate, potassium pyrophosphate, sodium metaborate, potassium metaborate, borax, ammonium hydroxide, tetramethyl ammonium, tetrabutyl ammonium, ammonia, MeNH₁ (Me represents CH₃ hereinafter), Me₂NH, EtNH₂ (Et represents C₂H₂ hereinafter), Et₂NH, C₄H₉NH₂, (C₄H₉)₂NH, HOC₂H₄NH₂, (HOC₂H₄)₂NH, Et₂NCH₂CH₂OH, H₂NC₂H₄NH₂, MeNHC₂H₄NHMe, Me₂NC₂H₄NH₂, H₂NC₃H₆NH₂, H₂NC₄H₈NH₂, H₂NC₅H₁₀NH₂, Me₂NC₂H₄NMe₂, Me₂NC₃H₆NMe₂,

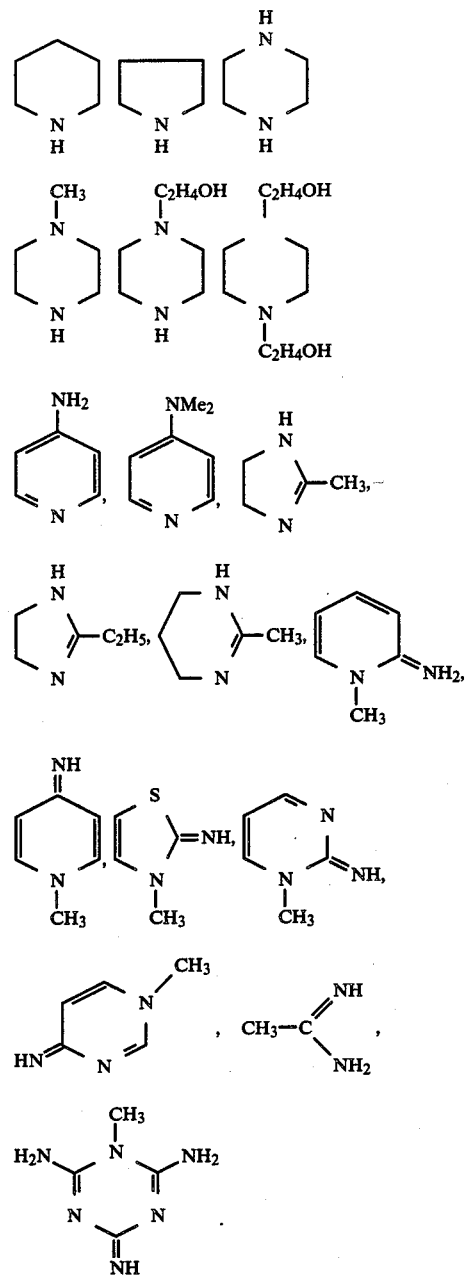

Specific examples of preferred base precursors are set forth below, but the present invention should not be construed as being limited thereto.

As trichloroacetic acid derivatives, there are guanidine trichloroacetic acid, piperidine trichloroacetic acid, morpholine trichloroacetic acid, p-toluidine trichloroacetic acid, 2-picoline trichloroacetic acid, etc. These compounds are believed to release a base by decarboxylation of the acid moiety.

In addition, base precursors as described in British Pat. No. 998,945, U.S. Pat. No. 3,220,846, Japanese Patent Application (OPI) No. 22625/75, etc., can be used.

As substances besides trichloroacetic acids, there are 2-carboxycarboxamide derivatives as described in U.S. Pat. No. 4,088,496, α-sulfonylacetate derivatives as described in U.S. Pat. No. 4,060,420, salts of propiolic acid derivatives and bases as described in Japanese Patent Application No. 55700/83, etc. Salts using alkali metal or an alkaline earth metal as a base component other than organic bases are also effective.

As other precursors, hydroxamic carbamates as described in Japanese Patent Application No. 43860/83 utilizing Lossen rearrangement and aldoxime carbamates as described in Japanese Patent Application No. 31614/83 which form a nitrile, etc., are effective.

Further, amineimides as described in *Research Disclosure*, No. 15776 (May, 1977) and aldonic amides as described in Japanese Patent Application (OPI) No. 22625/75 are suitably used, because they form a base by decomposition at a high temperature.

These bases and base precursors can be used over a wide range. An effective range is not more than 50% by weight based on the total weight of the dried coating layers on the support in the photosensitive material, and, preferably a range of from 0.01% by weight to 40% by weight.

The above-described bases or base precursors can be used not only for the acceleration of dye release but also for other purposes such as the control of a pH value.

The above-described various ingredients to constitute a heat developable photosensitive material can be arranged in arbitrary positions, if desired. For instance, one or more of the ingredients can be incorporated in one or more of the constituent layers of a photosensitive material, if desired. In some cases, it is desired that particular portions of reducing agent, image stabilizing agent and/or other additives should be distributed in a protective layer. As a result of the distribution in the above-described manner, migration of additives among constituent layers of a heat developable photosensitive material can be reduced. Therefore, such distribution of additives is of advantage to some cases.

The heat developable photosensitive materials of the present invention are effective in forming both negative or positive images. The negative or positive image can be formed depending mainly on the type of the light-sensitive silver halide. For instance, in order to produce direct positive images, internal image type silver halide emulsions described in U.S. Pat. Nos. 2,592,250, 3,206,313, 3,367,778 and 3,447,927, or mixtures of surface image type silver halide emulsions with internal image type silver halide emulsions as described in U.S. Pat. No. 2,996,382 can be used.

Various means of exposure can be used in the present invention. Latent images are obtained by imagewise exposure by radiant rays including visible rays. Generally, light sources used for conventional color prints can be used, example of which include tungsten lamps, mercury lamps, halogen lamps such as iodine lamps, xenon lamps, laser light sources, CRT light sources, fluorescent tubes and light-emitting diodes, etc.

In the present invention, after the heat-developable color photosensitive material is exposed to light, the resulting latent image can be developed by heating the whole material to a suitably elevated temperature. A higher temperature or lower temperature can be utilized to prolong or shorten the heating time, if it is within the above described temperature range.

As the heating means, a simple heat plate, iron, heat roller, heat generator utilizing carbon or titanium white, etc., or analogues thereof may be used.

A support used in the photosensitive material and the dye fixing material employed, if desired, according to the present invention is that which can endure at the processing temperature. As an ordinary support, not only glass, paper, metal or analogues thereof may be used, but also an acetyl cellulose film, a cellulose ester film, a polyvinyl acetal film, a polystyrene film, a polycarbonate film, a polyethylene terephthalate film, and a film related thereto or a plastic material may be used. Further, a paper support laminated with a polymer such as polyethylene, etc., can be used. The polyesters described in U.S. Pat. Nos. 3,634,089 and 3,725,070 are preferably used.

In the photosensitive material and the dye-fixing material of the present invention, the photographic emulsion layer and other binder layers may contain inorganic or organic hardeners. It is possible to use chromium salts (chromium alum, chromium acetate, etc.), aldehydes (formaldehyde, glyoxal, glutaraldehyde, etc.), N-methylol compounds (dimethylolurea, methylol dimethylhydantoin, etc.), dioxane derivatives (2,3-dihydroxydioxane, etc.), active vinyl compounds (1,3,5-triacryloyl-hexahydro-s-triazine, 1,3-vinylsulfonyl-2-propanol, etc.), active halogen compounds (2,4-dichloro-6-hydroxy-s-triazine, etc.), mucohalogenic acids (mucochloric acid, mucophenoxychloric acid, etc.), etc. which are used individually or as a combination thereof.

The transfer of dyes from the light-sensitive layer to the dye-fixing layer can be carried out using a dye transfer assistant.

The dye transfer assistants suitably used in a process wherein it is supplied from the outside include water and an aqueous solution containing sodium hydroxide, potassium hydroxide or an inorganic alkali metal salt. Further, a solvent having a low boiling point such as methanol, N,N-dimethylformamide, acetone, diisobutyl ketone, etc., and a mixture of such a solvent having a low boiling point with water or an alkaline aqueous solution can be used. The dye transfer assistant may be used by wetting the image receiving layer with the transfer assistant.

When the dye transfer assistant is incorporated into the photosensitive material or the dye-fixing material, it is not necessary to supply the transfer assistant from the outside. In this case, the above described dye transfer assistant may be incorporated into the material in the form of water or crystallization or microcapsules or as a precursor which releases a solvent at a high temperature.

More preferred process is a process wherein a hydrophilic thermal solvent which is solid at an ambient temperature and melts at a high temperature is incorporated into the photosensitive material or the dye-fixing material. The hydrophilic thermal solvent can be incorporated either into any of the photosensitive material and the dye-fixing material or into both of them. Although the solvent can be incorporated into any of the emulsion layer, the intermediate layer; the protective layer and the dye-fixing layer, it is preferred to incorporate it into the dye-fixing layer and/or adjacent layers thereto.

Examples of the hydrophilic thermal solvents include ureas, pyridines, amides, sulfonamides, imides, alcohols, oximes and other heterocyclic compounds.

Other compounds which can be used in the photosensitive material of the present invention, for example, sulfamide derivatives, cationic compounds containing a pyridinium group, surface active agents having polyethylene oxide chains, sensitizing dye, antihalation and anti-irradiation dyes, hardeners, mordants and so on, are those described in U.S. Pat. Nos. 4,500,626, 4,478,927 and 4,463,079, and Japanese Patent Application No. 28928/83 (corresponding to U.S. patent application Ser. No. 582,655 filed on Feb. 23, 1984) and U.S. Pat. No. 4,503,137. Methods for the exposure and so on cited in the above described patents can be employed in the present invention also.

The heat developable photosensitive material of the present invention is extremely excellent in maintaining its freshness during storage because a base precursor which does not exhibit basic character before development and has high stability at ordinary temperatures is employed to provide the basic component at the time of development. In addition, since the base precursor is decomposed rapidly by heating to release its base moiety, the heat developable photosensitive material of the present invention can provide a high quality image having high density by rapid development.

The present invention will now be illustrated in more detail by reference to the following examples. However, the present invention should not be construed as in any way being limited to the following examples. Unless otherwise indicated, all parts, percents and ratios are by weight.

EXAMPLE 1

A silver iodobromide emulsion was prepared in the following manner.

A solution containing 40 g of gelatin and 26 g of KBr dissolved in 3,000 ml of water was kept at 50° C. with stirring while a solution containing 34 g of silver nitrate dissolved in 200 ml of water and a 200 ml portion of the solution prepared by dissolving 0.02 g of Dye (1) illustrated below in 300 ml of methanol were added thereto simultaneously over a 10-minute period. Then, a solution containing 3.3 g of potassium iodide dissolved in 100 ml of water was further added to the resulting solution over a 2-minute period.

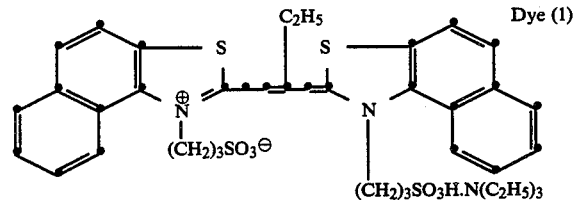
Dye (1)

The thus prepared silver iodobromide emulsion was adjusted to a proper pH value to cause flocculation and thereby, unnecessary salts were removed from the emulsion. The resulting emulsion was adjusted to pH 6.0, to produce the desired silver iodobromide emulsion in a yield of 400 g.

A gelatin dispersion of a coupler was prepared in the following manner.

5 g of 2-dodecylcarbamoyl-1-naphthol, 0.5 g of sodium 2-ethyl-hexyl sulfosuccinate, and 2.5 g of tricresyl phosphate (TCP) were weighed out respectively, and admixed with 30 ml of ethyl acetate to prepare a solution. The solution was mixed with 100 g of a 10% aqueous gelatin solution with stirring, and dispersed over a period of 10 minutes using a homogenizer rotating at 10,000 rpm.

A photosensitive material was prepared in the following manner.

A coating composition prepared by adding one of the base precursors set forth in Table 1 to the composition made up of ingredients (a) to (d) described below was coated on a polyethylene terephthalate film support in a wet thickness of 60 μm, and then dried.

| (a) Silver Iodobromide Emulsion | 10 g |
|---|---|
| (b) Gelatin Dispersion of Coupler | 3.5 g |
| (c) Gelatin (10% aqueous solution) | 5 g |
| (d) Solution containing 0.2 g of 2,6-Dichloro-p-aminophenol dissolved in 17 ml of water | |

The thus produced photosensitive materials were imagewise exposed for 5 seconds under an illuminance of 2,000 lux using a tungsten lamp and then heated uniformly for 20 seconds on a heat block heated to 150° C. to produce a negative cyan image. Separately, another sample of each photosensitive material was kept at 60° C. for 2 days, and then exposed and developed as described above to produce a negative cyan image. Densities of these images were measured using a Macbeth transmission densitometer (TD-504). The results shown in Table 1 were obtained.

TABLE 1

| Base Precursor No. | Amount Added | Fresh Dmax | Fresh Dmin | After 60° C. for 2 days Dmax | After 60° C. for 2 days Dmin |
|---|---|---|---|---|---|
| 3 (Invention) | 0.25 g | 1.90 | 0.13 | 1.83 | 0.15 |
| 4 (Invention) | 0.28 g | 2.08 | 0.14 | 2.03 | 0.19 |
| 8 (Invention) | 0.30 g | 1.89 | 0.11 | 1.84 | 0.18 |
| 19 (Invention) | 0.36 g | 2.16 | 0.15 | 2.09 | 0.21 |
| Comparison | 0.18 g | 2.20 | 0.18 | 2.15 | 1.85 |

The base precursor used for comparison in the above table was the compound represented by the following formula,

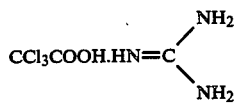

These results demonstrate that the use of the base precursor of the present invention can effect a great improvement in the storage quality of the photosensitive material.

EXAMPLE 2

In preparing a photosensitive material, the same silver iodobromide emulsion as used in Example 1 and the following dispersion of a dye providing substance were employed.

The dispersion of the dye providing substance was prepared in the following manner.

5 g of the dye providing substance (2) having the structural formula illustrated in this specification, 0.5 g of sodium 2-ethyl-hexyl sulfosuccinate and 5 g of tricresyl phosphate were weighed out respectively, and they were admixed with 30 ml of ethyl acetate. The mixture was heated up to about 60° C. and thereby it was converted into a homogeneous solution. This solution was mixed with 100 g of a 10% aqueous gelatin solution with stirring, and further dispersed for 10 minutes using a homogenizer rotating at 10,000 rpm.

A photosensitive material was produced in the following manner.

| | | |
|---|---|---|
| (a) | Light-sensitive Silver Iodobromide Emulsion (the same as produced in Example 1) | 25 g |
| (b) | Dispersion of Dye providing Substance (2) | 33 g |
| (c) | 5% Aqueous Solution of Compound having the following structural formula: | 10 ml |

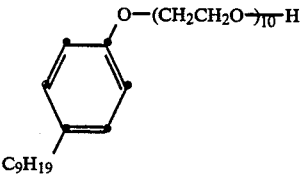

| | | |
|---|---|---|
| (d) | 10% Aqueous solution of Compound having the following structural formula: $H_2N-SO_2-N(CH_3)_2$ | 4 ml |
| (e) | Water | 20 ml |

A coating composition was prepared by admixing one of the base precursors set forth in the following Table 2 with the ingredients (a) to (e) described above, and heating the resulting mixture to convert into a homogeneous state. It was coated on a polyethylene terephthalate film support in a wet thickness of 30 μm, and dried. Each of the thus obtained samples was imagewise exposed for 10 seconds at an illuminance of 2,000 lux using a tungsten lamp. Thereafter, each sample was heated uniformly for 20 seconds on a heat block heated to 150° C.

Separately, an image receiving material having an image-receiving layer was prepared in the following manner.

In 200 ml of water was dissolved 10 g of methylacrylate/N,N,N-trimethyl-N-vinylbenzylammonium chloride copolymer in wich the copolymerizing ratio of the former monomer to the latter monomer was 1:1). The solution was mixed homogeneously with 100 g of 10% lime-processed gelatin solution. The resulting mixture was coated uniformly in a wet thickness of 90 μm on a paper support laminated with polyethylene into which titanium oxide had been dispersed. After drying, the thus obtained material was used as an image-receiving material.

After being dipped in water, the image-receiving material was superposed on the exposed, heated photosensitive material in face-to-face contact. The superposed materials were heated on a heat block at 80° C. for 60 seconds and then the image receiving material was peeled off the photosensitive material, to produce a negative magenta dye image on the image receiving material. Separately, another wet sample of the image receiving material was superposed on a sample of a photosensitive materials, prepared as described above but which had been kept at 60° C. for 2 days after preparation and then had been exposed and heated as described above, and the superposed materials were processed as described above to produce a negative magenta dye image on the image receiving material. Densities of these negative images were measured with a Macbeth reflection densitometer (RD-519), to obtain the results shown in Table 2.

TABLE 2

| Base Precursor No. | Amount Added | Fresh Dmax | Fresh Dmin | After 60° C. for 2 days Dmax | After 60° C. for 2 days Dmin |
|---|---|---|---|---|---|
| 3 (Invention) | 2.5 g | 1.88 | 0.14 | 1.81 | 0.19 |
| 4 (Invention) | 2.8 g | 2.09 | 0.16 | 2.01 | 0.20 |
| 8 (Invention) | 3.0 g | 1.92 | 0.14 | 1.81 | 0.21 |
| 19 (Invention) | 3.6 g | 2.16 | 0.18 | 2.09 | 0.24 |
| Comparison | 1.8 g | 2.20 | 0.18 | 2.15 | 1.85 |

The base precursor used for comparison in the above table was the same as used for comparison in Table 1.

These results demonstrate that photosensitive materials according to the present invention provide excellent results for transfer of image dyes into an image receiving material, even after storage.

EXAMPLE 3

A photosensitive material in which an organic silver salt oxidizing agent is incorporated was prepared as illustrated below.

A benzotriazole silver emulsion was prepared in the following manner.

A solution prepared by dissolving 28 g of gelatin and 13.2 g of benzotriazole in 3,000 ml of water was kept at 40° C. with stirring while a solution containing 17 g of silver nitrate dissolved in 100 ml of water was added over a 2-minute period. Then pH control and precipitant addition were carried out to cause flocculation and thereby the excess salt was removed from the emulsion. The resulting emulsion was adjusted to pH 6.0. Thus, the desired benzotriazole silver emulsion was obtained in a yield of 400 g.

A light-sensitive coating composition was prepared using the thus obtained benzotriazole silver emulsion and the following ingredients.

| | | |
|---|---|---|
| (a) | Silver Iodobromide Emulsion (the same as prepared in Example 1) | 20 g |
| (b) | Benzotriazole Silver Emulsion | 10 g |
| (c) | Dispersion of Dye providing Substance (the same as described in Example 2) | 33 g |
| (d) | 5% Aqueous Solution of Compound having the following structural formula: | 10 ml |

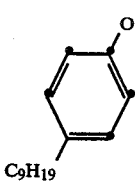

| | | |
|---|---|---|
| (e) | 10% Aqueous Solution of Compound having the following structural formula: $H_2NSO_2N(CH_3)_2$ | 4 ml |
| (f) | Present Base Precursor (3) | 3 g |
| (g) | Gelatin Dispersion of an Acid Precursor prepared in the manner described below | 8 ml |
| (h) | Water | 12 ml |

The gelatin dispersion of an acid precursor, which corresponds to ingredient (g), was prepared as follows.

10 g of a compound having the structural formula illustrated below was added to 100 g of a 1% aqueous solution of gelatin, and ground into fine particles over a 10-minute period during a mill having 100 g of glass beads. The glass beads used had a mean particle diameter of about 0.6 mm. Then, the glass beads were filtered out, and the desired gelatin-acid precursor dispersion was obtained.

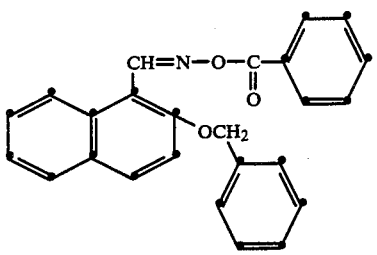

After mixing all of the above-described ingredients (a) to (h), samples were prepared and processed in the same manner as employed in Example 2. The results obtained are as follows.

| Sensitive Material | Fresh | | After 60° C. for 2 days | |
| --- | --- | --- | --- | --- |
| | Dmax | Dmin | Dmax | Dmin |
| Image Density | 2.03 | 0.15 | 2.00 | 0.24 |

These results have proved that the photosensitive material of the present invention containing an organic silver salt oxidant is also extremely excellent in storage quality.

EXAMPLE 4

A benzotraizole silver emulsion containing light-sensitive silver bromide was prepared in the following manner.

10 g of gelatin and 6.5 g of benzotriazole were dissolved in 1,000 ml of water, and the resulting solution was kept at 50° C. with stirring while 8.5 g of silver nitrate dissolved in 100 ml of water was added over a 2-minute period.

Then, a solution containing 1.2 g of potassium bromide dissolved in 50 ml of water was further added over a 2-minute period. From the thus prepared emulsion were removed excess salts through flocculation caused by pH control. Then, the emulsion was adjusted to pH 6.0, to produce the desired benzotriazole silver emulsion in a yield of 200 g.

A gelatin dispersion of a dye providing substance was prepared as follows.

10 g of a dye providing substance having the structural formula illustrated below, 0.5 g of sodium 2-ethylhexyl sulfosuccinate acting as a surface active agent, and 4 g of tricresyl phosphate were weighed out, and they were admixed with 20 ml of cyclohexanone and heated to about 60° C., to produce a homogeneous solution. This solution was mixed with 100 g of a 10% lime-processed gelatin solution with stirring, and dispersed for 10 minutes using a homogenizer rotating at 10,000 rpm.

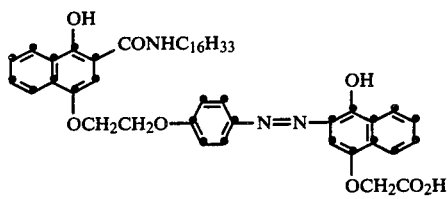

A photosensitive material was produced in the following manner.

| (a) | Benzotriazole Silver Emulsion containing Light-sensitive Silver Bromide | 10 g |
| --- | --- | --- |
| (b) | Dispersion of Dye providing Substance | 3.5 g |
| (c) | Present Base Precursor (3) | 0.34 g |
| (d) | Gelatin (10% aqueous solution) | 5 g |
| (e) | Solution prepared by dissolving 200 mg of 2,6-dichloro-4-aminophenol in 4 ml of methanol | |

The above-described ingredients (a) to (e) were all mixed, and dissolved by heating. The resulting solution was coated on a 180 $\mu$-thick polyethylene terephthalate film in a wet thickness of 30 $\mu$m. After drying, the sample was imagewise exposed for 5 seconds at an illuminance of 2,000 lux using a tungsten lamp, and then heated uniformly for 20 seconds on a heat block heated to 150° C.

The thus processed sample was used together with the same image receiving material as employed in Example 2, and subjected to the same processing as the freshly-prepared sample in Example 2, to produce negative magenta image on the image receiving material. The density of this negative image was measured with a Macbeth reflection densitometer (RD-519). The maximum density of the image was 1.75, and the minimum density thereof was 0.17.

These results have proved that the compound of the present invention has an excellent effect.

EXAMPLE 5

A gelatin dispersion of a dye providing substance was prepared as follows.

5 g of a dye releasing agent having the following structural formula, which is subject to reduction,

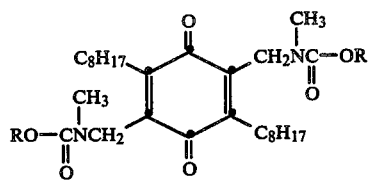

(wherein R represents

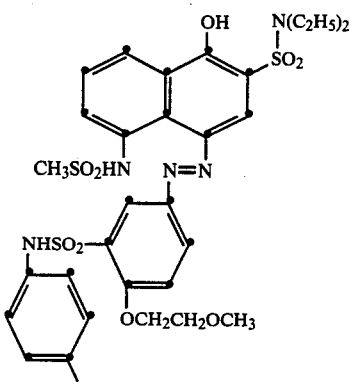

4 g of an electron donative substance having the following structural formula:

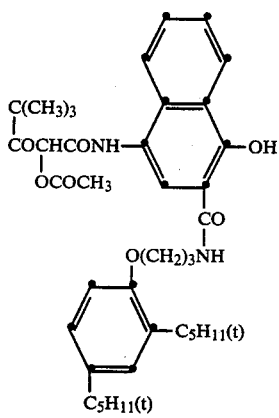

0.5 g of sodium 2-ethyl-hexyl sulfosuccinate and 10 g of tricresyl phosphate (TCP) were weighed out and mixed. Thereto, 20 ml of cyclohexanone was added. The resulting mixture was heated at about 60° C. and thereby was converted into a homogeneous solution. This solution was mixed with 100 g of a 10% aqueous gelatin solution with stirring, and dispersed for 10 minutes using a homogenizer rotating at 10,000 rpm.

| A photosensitive material was prepared as follows. | |
|---|---|
| (a) Benzotriazole Silver Emulsion containing Light-sensitive Silver Bromide (the same described in Example 4) | 10 g |
| (b) Dispersion of Dye providing Substance prepared in this Example | 3.5 g |
| (c) Present Base Precursor (3) | 0.48 g |
| (d) 5% Aqueous Solution of a Compound having the following structural formula: 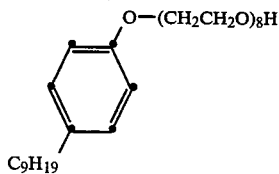 | 1.5 ml |

With the above-described ingredients (a) to (d) was admixed 4 ml of water. The resulting mixture was dissolved by heating, and coated on a polyethylene terephthalate film in a wet thickness of 30 μm, and dried, to produce the desired photosensitive material.

The photosensitive material obtained was imagewise exposed for 10 seconds at an illuminance of 2,000 lux using a tungsten lamp, and then heated uniformly for 40 seconds on a heat block heated to 140° C.

After being dipped in water, the same image receiving material as prepared in Example 2 was superposed on the photosensitive material heated in the above-described manner in face-to-face contact, the superposed material was heated on a heat block at 80° C. for 6 seconds and the image receiving material was peeled off the photosensitive material to produce a positive magenta image on the image receiving material. The density of the positive magenta image formed on the image receiving material was measured with a Macbeth reflection densitometer (RD-519). The maximum density of this image to green light was 1.71, and the minimum density thereof was 0.26.

This result demonstrates the effectiveness of the base precursor of the present invention.

While the invention has been described in detail and with reference to specific embodiments thereof, it will be apparent to one skilled in the art that various changes and modifications can be made therein without departing from the spirit and scope thereof.

What is claimed is:

1. A heat developable photosensitive material comprising a support having thereon at least one light-sensitive layer comprising light-sensitive silver halide and a binder, wherein at least one layer contains a base precursor represented by the following general formula (I):

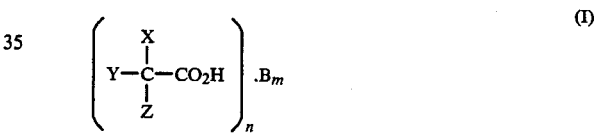

wherein at least one of X, Y and Z, which may be the same or different, represents an electron-attractive substituent selected from the group (a) consisting of a substituted sulfamoyl group, an unsubstituted sulfamoyl group, an

group and an

group, wherein R and $R_2$ each represents a hydrogen atoms, an alkyl group or an aryl group, and the alkyl or aryl moiety of these groups may be further substituted;

the remainder of X, Y and Z being selected from the group (b) consisting of a hydrogen atom, an alkyl group, a cycloalkyl group, an alkenyl group, an alkynyl group, an aryl group, an aralkyl group, a silyl group, an alkoxy group, an aryloxy group, an alkylthio group, an arylthio group and a hydroxy group, wherein the alkyl and aryl moieties may be further substituted with a substituent other than a perhaloalkyl group containing up to 3 carbon atoms;

B represents a mono-acidic or di-acidic base having a pKa value of at least 7 and containing not more than 12 carbon atoms; and n and m each represents 1 or 2, provided that the net charge of the compound is zero.

2. A heat-developable photosensitive material as claimed in claim 1, wherein the base moiety represented by B is an organic base having a pKa value of about 9 or more, a boiling point of at least about 100° C. and containing 10 or fewer carbon atoms.

3. A heat-developable photosensitive material as claimed in claim 2, wherein said base moiety is selected from the group consisting of a quanidine, a cyclic quanidine, an amidine, and a cyclic amidine.

4. A heat-developable photosensitive material as claimed in claim 1, wherein said base precursor constitutes up to about 50 wt% of the total dry weight of said light-sensitive layer.

5. A heat-developable photosensitive material as claimed in claim 4, wherein said base precursor constitutes from about 0.01 to about 40 wt% of the total dry weight of said light-sensitive layer.

6. A heat-developable photosensitive material as claimed in claim 1, wherein said light-sensitive layer further comprises an organic silver salt oxidizing agent.

7. A heat-developable photosensitive material as claimed in claim 1, wherein the electron-attractive substituent selected from the group (a) is said substituted sulfamoyl group.

8. A heat-developable photosensitive material as claimed in claim 1, wherein the electron-attractive substituent selected from the group (a) is said unsubstituted sulfamoyl group.

9. A heat-developable photosensitive material as claimed in claim 1, wherein the electron-attractive substituent selected from the group (a) is said

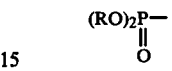

group.

10. A heat-developable photosensitive material as claimed in claim 1, wherein the electron-attractive substituent selected from the group (a) is said

group.

* * * * *